US010433861B2

(12) United States Patent
Feldman et al.

(10) Patent No.: US 10,433,861 B2
(45) Date of Patent: Oct. 8, 2019

(54) SYSTEM AND METHOD FOR CUTTING TRABECULAE CARNEAE OF THE LEFT VENTRICLE TO INCREASE LV COMPLIANCE

(71) Applicant: The Board of Regents of The University of Texas System, Austin, TX (US)

(72) Inventors: Marc D. Feldman, San Antonio, TX (US); Daniel Escobedo, San Antonio, TX (US); David L. Halaney, San Antonio, TX (US); Jordan C. Dwelle, San Antonio, TX (US); Austin B. McElroy, San Antonio, TX (US); Thomas E. Milner, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 576 days.

(21) Appl. No.: 14/915,394

(22) PCT Filed: Aug. 27, 2014

(86) PCT No.: PCT/US2014/052903
§ 371 (c)(1),
(2) Date: Feb. 29, 2016

(87) PCT Pub. No.: WO2015/031476
PCT Pub. Date: Mar. 5, 2015

(65) Prior Publication Data
US 2016/0213393 A1    Jul. 28, 2016

Related U.S. Application Data

(60) Provisional application No. 61/870,533, filed on Aug. 27, 2013.

(51) Int. Cl.
*A61B 18/20* (2006.01)
*A61B 17/32* (2006.01)
(Continued)

(52) U.S. Cl.
CPC ...... *A61B 17/320016* (2013.01); *A61B 18/22* (2013.01); *A61B 18/24* (2013.01);
(Continued)

(58) Field of Classification Search
CPC .......................... A61B 18/20; A61B 2018/003
(Continued)

(56) References Cited

U.S. PATENT DOCUMENTS 5,195,956 A    3/1993   Stockmeier
5,295,958 A    3/1994   Shturman
(Continued)

FOREIGN PATENT DOCUMENTS

WO    95/15715    6/1995
WO    9635469     11/1996
(Continued)

OTHER PUBLICATIONS

International Search Report and Written Opinion for PCT/US2014/052903 dated Feb. 6, 2015.
(Continued)

*Primary Examiner* — Lynsey C Eiseman
(74) *Attorney, Agent, or Firm* — Meyertons, Hood, Kivlin, Kowert & Goetzel, P.C.

(57) ABSTRACT

In some embodiments, a method of ameliorating diastolic dysfunction may include positioning at least a distal end of a system for cutting a trabeculae carneae in a left ventricle of a human heart. The system may include an elongated member, a grip, an engaging portion, and a cutting device. A second end of the engaging portion may turn in upon the engaging portion towards a first end of the engaging portion
(Continued)

while still allowing trabeculae carneae to enter through an opening between the first and second ends. The cutting device may be positioned within an inner diameter of the engaging portion. The method may include positioning at least one trabeculae carneae in the inner diameter of the engaging portion. The method may include severing the at least one trabeculae carneae. The method may include increasing left ventricular compliance of the human heart.

5 Claims, 12 Drawing Sheets

(51) Int. Cl.
 *A61B 18/22* (2006.01)
 *A61B 18/24* (2006.01)
 *A61B 17/00* (2006.01)
 *A61B 18/00* (2006.01)

(52) U.S. Cl.
 CPC ........... *A61B 2017/00243* (2013.01); *A61B 2017/00539* (2013.01); *A61B 2017/32004* (2013.01); *A61B 2018/00351* (2013.01); *A61B 2018/00357* (2013.01); *A61B 2018/2238* (2013.01); *A61B 2018/2261* (2013.01); *A61B 2018/2266* (2013.01)

(58) Field of Classification Search
 USPC ...................................... 606/2–19
 See application file for complete search history.

(56) References Cited

U.S. PATENT DOCUMENTS

| | | | |
|---|---|---|---|
| 5,370,134 A | | 12/1994 | Chin et al. |
| 5,397,333 A | | 3/1995 | Knoepfler |
| 5,655,548 A | | 8/1997 | Nelson et al. |
| 5,695,511 A | | 12/1997 | Cano et al. |
| 5,755,714 A | * | 5/1998 | Murphy-Chutorian ................ A61B 18/24 606/15 |
| 5,824,071 A | | 10/1998 | Nelson et al. |
| 5,855,614 A | | 1/1999 | Stevens et al. |
| 5,931,848 A | | 8/1999 | Saadat |
| 5,972,030 A | | 10/1999 | Garrison et al. |
| 6,051,008 A | | 4/2000 | Saadat et al. |
| 6,056,743 A | | 5/2000 | Ellis et al. |
| 6,080,175 A | | 6/2000 | Hogendijk |
| 6,125,852 A | | 10/2000 | Stevens et al. |
| 6,165,188 A | | 12/2000 | Saadat et al. |
| 6,251,104 B1 | | 6/2001 | Kesten |
| 6,254,621 B1 | | 7/2001 | Shackelford et al. |
| 6,387,108 B1 | | 5/2002 | Taylor et al. |
| 6,447,539 B1 | | 9/2002 | Nelson et al. |
| 6,514,248 B1 | | 2/2003 | Eggers et al. |
| 6,638,235 B2 | | 10/2003 | Miller et al. |
| 6,681,773 B2 | | 1/2004 | Murphy et al. |
| 6,796,963 B2 | | 9/2004 | Carpenter et al. |
| 6,802,319 B2 | | 10/2004 | Stevens et al. |
| 6,899,704 B2 | | 5/2005 | Sterman et al. |
| 6,959,711 B2 | | 11/2005 | Murphy et al. |
| 7,101,402 B2 | | 9/2006 | Phelps et al. |
| 7,186,210 B2 | | 3/2007 | Feld et al. |
| 7,255,706 B2 | | 8/2007 | Rosengart |
| 7,335,158 B2 | | 2/2008 | Taylor |
| 7,470,272 B2 | | 12/2008 | Mulier et al. |
| 7,485,088 B2 | | 2/2009 | Murphy et al. |
| 7,485,090 B2 | | 2/2009 | Taylor |
| 7,513,867 B2 | | 4/2009 | Lichtenstein |
| 7,520,886 B2 | | 4/2009 | Surti |
| 7,608,091 B2 | | 10/2009 | Goldfarb et al. |
| 8,292,884 B2 | | 10/2012 | Levine et al. |
| 2002/0029783 A1 | | 3/2002 | Stevens et al. |
| 2002/0068924 A1 | * | 6/2002 | Sinofsky ................ A61B 18/22 606/3 |
| 2002/0193782 A1 | | 12/2002 | Ellis |
| 2003/0102000 A1 | | 6/2003 | Stevens et al. |
| 2004/0002626 A1 | | 1/2004 | Feld et al. |
| 2004/0034380 A1 | | 2/2004 | Woolfson et al. |
| 2004/0193191 A1 | | 9/2004 | Starksen et al. |
| 2005/0197693 A1 | | 9/2005 | Pai et al. |
| 2005/0288654 A1 | | 12/2005 | Niemen et al. |
| 2006/0095025 A1 | | 5/2006 | Levine et al. |
| 2007/0010812 A1 | | 1/2007 | Mittelstein et al. |
| 2007/0073274 A1 | | 3/2007 | Chin et al. |
| 2008/0015466 A1 | | 1/2008 | Lerman |
| 2008/0234728 A1 | | 9/2008 | Starksen et al. |
| 2009/0069888 A1 | | 3/2009 | Drake |
| 2009/0149872 A1 | | 6/2009 | Gross |
| 2009/0287143 A1 | | 11/2009 | Line |
| 2009/0306582 A1 | | 12/2009 | Granada et al. |
| 2011/0118769 A1 | | 5/2011 | Bliss et al. |
| 2012/0041500 A1 | | 2/2012 | Zhu et al. |
| 2013/0103047 A1 | | 4/2013 | Steingisser et al. |

FOREIGN PATENT DOCUMENTS

| | | |
|---|---|---|
| WO | 2011060386 | 5/2011 |
| WO | 2014055981 | 4/2014 |
| WO | 2015031476 | 3/2015 |

OTHER PUBLICATIONS

International Preliminary Report on Patentability for PCT/US2014/052903 dated Mar. 1, 2016.
International Preliminary Report on Patentability from PCT/US2013/063701, dated Apr. 16, 2015, Board of Regents, The University of Texas System, pp. 1-10.
Non Final Office Action for U.S. Appl. No. 14/433,763 dated May 19, 2017.
Final Office Action for U.S. Appl. No. 14/433,763 dated May 2, 2018.
Non Final Office Action for U.S. Appl. No. 14/433,763 dated Dec. 14, 2018.

* cited by examiner

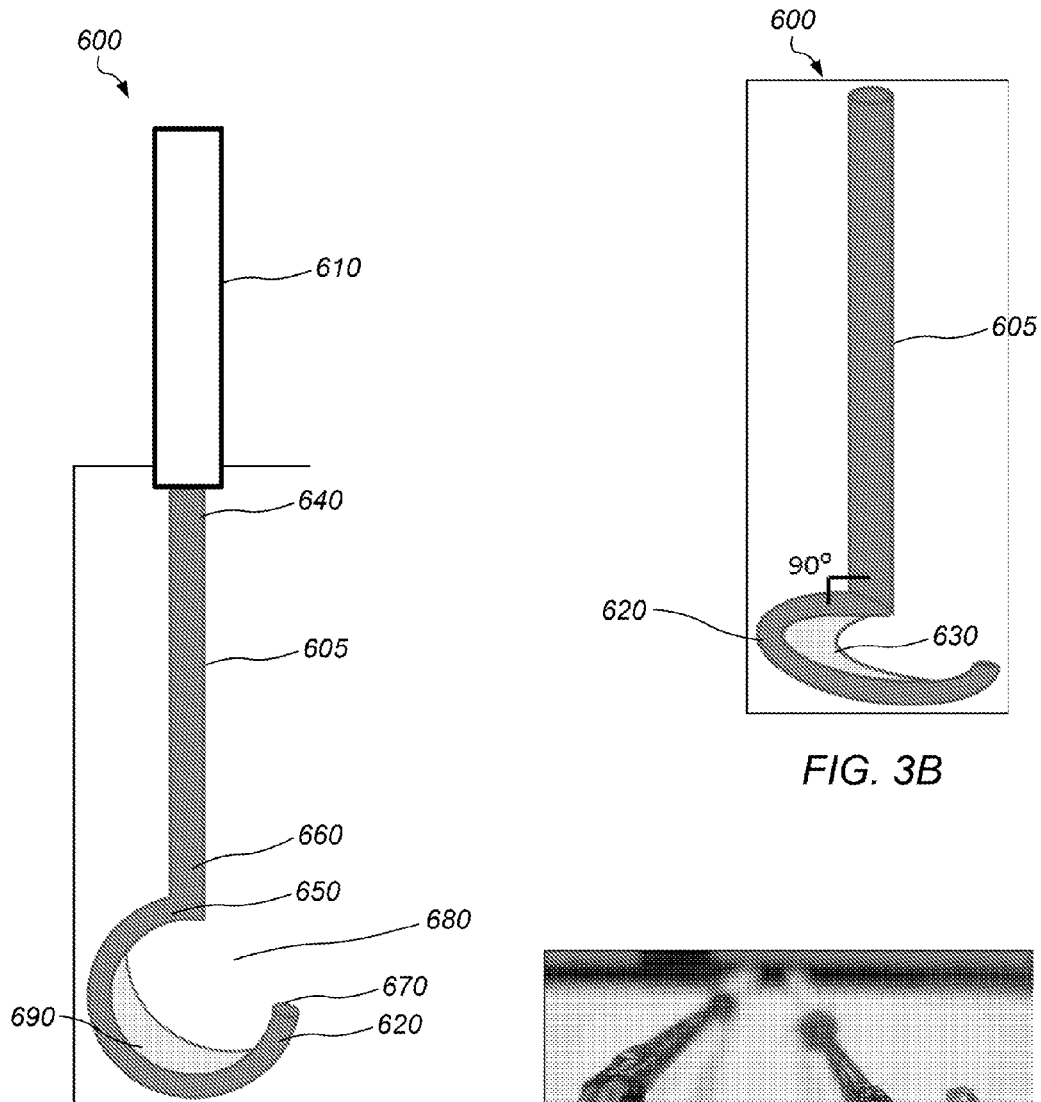
FIG. 3A
FIG. 3B
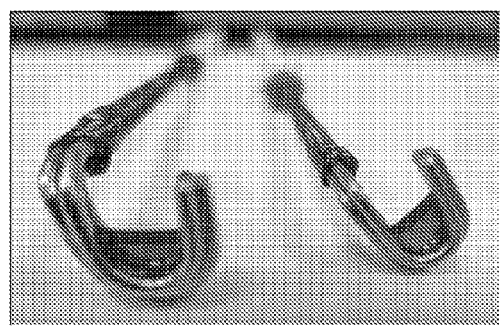
FIG. 3C
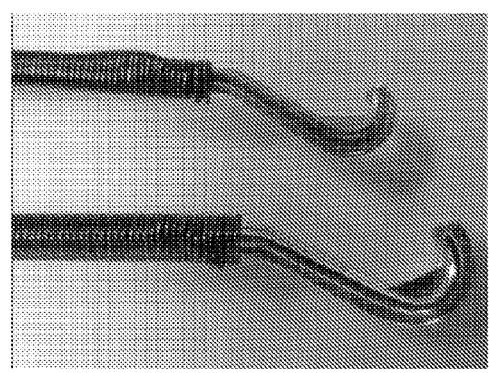
FIG. 3D

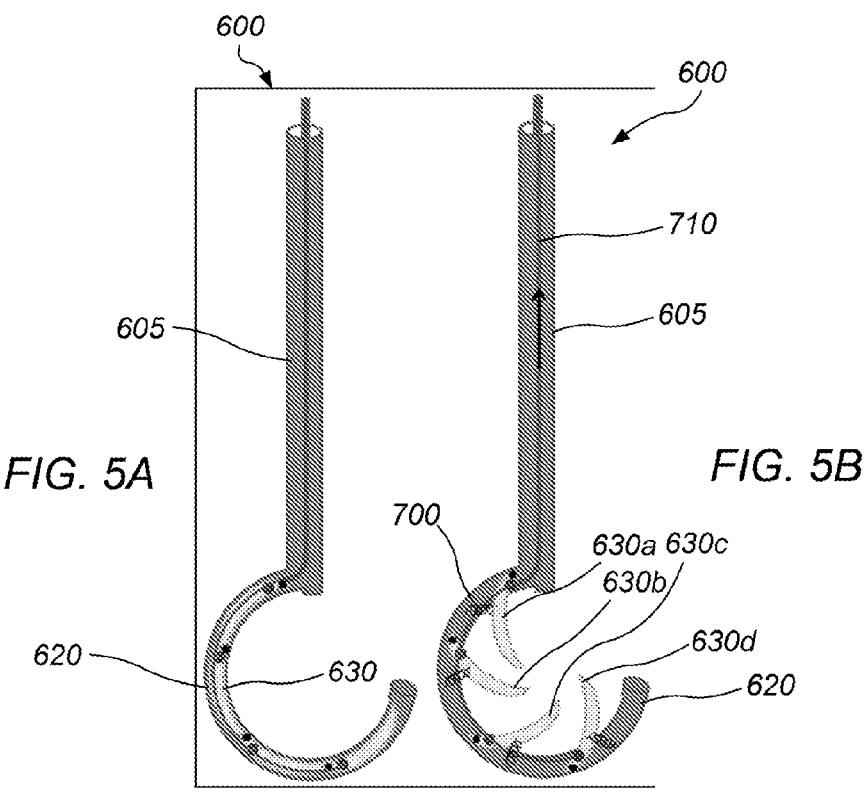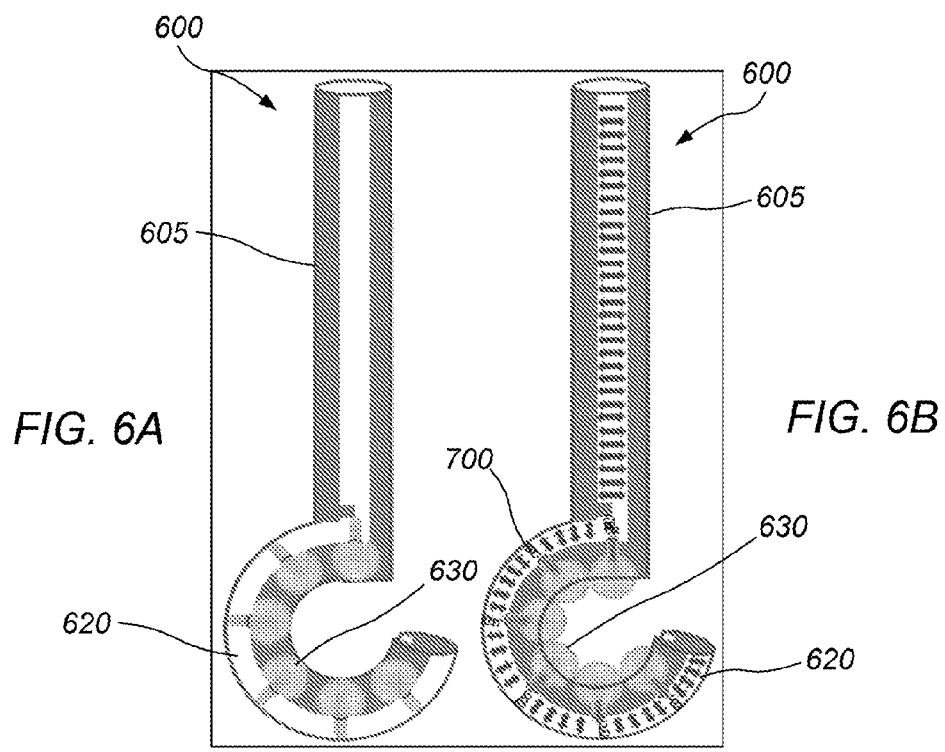

SYSTEM AND METHOD FOR CUTTING TRABECULAE CARNEAE OF THE LEFT VENTRICLE TO INCREASE LV COMPLIANCE

BACKGROUND OF THE INVENTION

1. Field of the Invention

The present disclosure generally relates to increasing left ventricular compliance. More particularly, the disclosure generally relates to systems and methods for cutting trabeculae carneae in order to increase left ventricular compliance.

2. Description of the Relevant Art

Left ventricular (LV) diastolic dysfunction (reduced compliance) was first identified in the 1970s as an important etiology producing shortness of breath in patients at rest and exertion, and as a major cause of hospital admission due to diastolic heart failure. Half of all heart failure admissions are due to left ventricular systolic failure (enlarged weak hearts), but half are caused by hearts with normal systolic function that are thickened with diastolic dysfunction. Despite 40 years developing solutions to improve left ventricular diastolic compliance, there have been no mediations or therapies invented which can acutely and permanently increase compliance. Medications which reduce calcium availability to the myocytes have not successfully improved diastolic compliance. As a result, medications are being used to slow the heart rate to prolong diastole (calcium and beta blockers), or decrease left ventricular filling pressures by moving down a fixed compliance curve with diuretics to reduce blood volume. However, there are no medications which can improve left ventricular diastolic compliance. That is because left ventricular compliance is known to be primarily related to the thickness of the left ventricular myocardium (normally 8-9 mm and increases to 12-16 mm) and the increase in the percentage of fibrosis which is known to occur as left ventricular hypertrophy develops (3% up to 12%). A genetic heart muscle condition called hypertrophic cardiomyopathy exists wherein a patient's heart can be as thick as 40 mm and the percentage of fibrosis can exceed more than 20% of the mass of the left ventricle.

The only therapeutic intervention currently available is the use of pharmacologicals to lower blood pressure in cases of left ventricular hypertrophy due to hypertension. However, although left ventricular hypertrophy can regress over months of time with normalization of blood pressure, left ventricular hypertrophy often cannot be completely normalized and often results in an increase in the percentage of fibrosis of the myocardium. Many other etiologies for left ventricular hypertrophy besides hypertension are recognized including diabetes, valvular heart disease, and hypertrophic cardiomyopathy. The relevant patient population is very large both in the U.S. (millions), and around the world.

While understanding of the human heart and the causes of diastolic dysfunction, from embryologic morphogenesis to normal and pathological function has advanced greatly over recent years, one feature, the trabeculae carneae, has received little attention. During embryologic morphogenesis of the heart, trabeculae carneae are some of the first features to arise in the developing cardiac tube (Bartram, *Pediatr Cardiol* 2007, 28:325-32). It is believed that the increased surface area afforded by these trabeculations facilitates diffusion, which is the primary means of nutrient acquisition by the developing cardiac tissue in lieu of a coronary system, which develops later in gestation (Bartram, *Pediatr Cardiol* 2007, 28:325-32). In parallel to the development of the coronary system, the trabeculae carneae undergo a process known as compaction, in which trabeculae carneae condense to form the myocardium (Bartram, *Pediatr Cardiol* 2007, 28:325-32). It has been proposed that the large intertrabecular spaces are transformed into capillaries during compaction (Gambetta, *Pediatr Cardiol* 2008, 29(2):434-7). Other structures of the heart are also thought to form from trabeculae carneae, such as the papillary muscles and chordae tendineae, as well as the inter-ventricular septum (Wenink, *Br Heart J* 1982, 48:462-8). In the human, not all trabeculae carneae are lost during development; trabeculations are still present in the apex and free-wall of the normal adult left ventricle (LV), and to a greater extent in the right ventricle (RV). The belief that these remaining trabeculae carneae are embryologic remnants (Wenink, *Br Heart J* 1982, 48:462-8) may explain why they have received little attention by the scientific community.

Although there has been little interest in the functional role of trabeculae carneae in the adult heart and their contribution to diastolic dysfunction, a few hypotheses have been proposed. One theory is that trabeculae carneae function to aid in systolic contraction by slowing incoming blood during diastole, thus reducing the kinetic energy that would otherwise have to be overcome during contraction (Burch, *Am Heart J* 1975, 89(2):261), (Burch, *Angiology* 1982, 33(4):221-7). Another theory is that the trabeculae carneae serve a nutritional role, directing blood flow to the papillary muscles and nodal conducting tissue within the heart (Taylor, *Can J Cardiol* 1999, 15(8):859-66). A final theory holds that trabeculae carneae serve the dual role of aiding in the force of systolic contraction through their own contractions and reducing residual blood volume at end-systole, as the intertrabecular spaces are reduced in size during contraction, forcing blood out of these spaces (Burch, *Circulation* 1952, 5:504-13). The scarcity of proposed functions of ventricular trabeculae carneae and the lack of empirical support for these theories evince that trabeculae carneae are poorly understood. Further, these proposed mechanisms are specious and are not consistent with a more recent understanding of the cardiovascular system.

Despite this lack of interest in trabecular function and their contribution to diastolic dysfunction, some attention has been paid to differences in trabeculae carneae between healthy hearts and several cardiovascular pathologies. The most drastic example is Left Ventricular Non-compaction (LVNC) or "Spongy Myocardium", characterized by a layer of prominent trabeculae carneae and deep intertrabecular recesses which is at least twice as thick as the outer compacted layer of myocardium (Franqui-Rivera, *P R Health Sci J* 2008, 27(4):377-81). This disease is believed to be the result of an intrauterine arrest to the normal compaction of the trabeculae carneae during cardiac morphogenesis, although this model has been challenged due to the observation of "acquired LVNC" in adults with originally normal hearts (Franqui-Rivera, *P R Health Sci J* 2008, 27(4):377-81). Importantly, LVNC has been documented associated with cardiac abnormalities that promote high intracavitary ventricular pressures (Franqui-Rivera, *P R Health Sci J* 2008, 27(4):377-81). While this condition is extremely rare, several more common pathologies exist with such prominent ventricular trabeculations that they are often mistaken for LVNC (Franqui-Rivera, *P R Health Sci J* 2008, 27(4):377-81). Left ventricular hypertrabeculation (LVHT) is a distinct disorder from LVNC, and may occur in patients with neuromuscular disorders (Stollberger, *Am J Cardiol* 2002, 90:899-902). Dilated cardiomyopathy, acquired left ventricular hypertrophy secondary to systemic hypertension, and left-sided obstructive congenital cardiac malformations are also known to present with prominent trabeculae carneae (Bartram, *Pediatr Cardiol* 2007, 28:325-32). In addition to these pathologies where trabeculae careneae are enlarged, trabeculae carneae are also known to become fibrotic in heart-failure; the fibrotic content of trabeculae carneae has been found to be up to 2.1 fold greater in failing hearts as compared to non-failing hearts (Gruver, *Basic Res Cardiol* 1994, 89(2):139-48).

There have been more recent efforts to explain diastolic dysfunction on a molecular level. In the mammalian left ventricle, the diastolic pressure-volume relationship increases exponentially. This exponential relationship is believed to be an intrinsic property of cardiac tissue and has recently been attributed to the sarcomeric protein titin. Titin is the largest protein in the body, extending half the length of a sarcomere from the M-line to the Z-disc, where it functions as a bidirectional molecular spring which maintains the physiologic sarcomere slack length of ≈1.9 μm. Titin contains an extensible region which, in the absence of external force, maintains a folded conformation (Granzier, *Circ Res* 2004, 94:284-95). The extensible region is composed of three types of segments: the Ig segments, the PEVK segment, and the N2B segment. As the extensible region is stretched during diastole, these different segments extend at different sarcomere lengths, resulting in a unique passive force-extension relationship that generates mild resistance to stretch close to the slack length and greater resistance to stretch at further distances from the slack length (Granzier, *Circ Res* 2004, 94:284-95). In mammalian cardiac titan, the N2B segment is found in two isoforms denoted N2B and N2BA. The N2BA isoform contains the N2B segment, but also an additional N2A segment, which results in additional extensibility of the titin molecule consistent with a more compliant LV during diastolic filling. Therefore cardiac myocytes that express high levels of N2B titin have higher passive stiffness than myocytes that express N2BA titin (Granzier, *Circ Res* 2004, 94:284-95). Mammalian species express one or both cardiac titin isoforms, and the relative amounts of each isoform vary greatly between species. Importantly, the ratio of titin isoforms is not fixed, and undergoes changes in response to chronic mechanical loading of the heart (Granzier, *Circ Res* 2004, 94:284-95). For instance, titin isoform switching is likely a contributor to diastolic dysfunction, as van Heerebeek et al. found that the titin N2BA/N2B ratio was lower in the myocardium of patients with diastolic heart failure (17/83) than in patients with systolic heart failure (35/65) (Van Heerebeek, *Circulation* 2006, 113:1966-73).

Despite the large role that titin is believed to play in determining passive myocardial stiffness, it is only part of the picture. Other factors such as myocyte hypertrophy, and the amount of collagen, the abundance of collagen type 1, and collagen cross-linking in the extracellular matrix also likely contribute to the increased myocardial stiffness characteristic of diastolic dysfunction (Borlaug, *Eur Heart J* 2011, 32:670-9).

Therefore a system and/or method which results in increase in left ventricular compliance is highly beneficial.

SUMMARY

This disclosure describes systems and methods for, in some embodiments, ameliorating diastolic dysfunction may include positioning at least a distal end of a system for cutting a trabeculae carneae in a left ventricle of a human heart. The system may include an elongated member, a grip, an engaging portion, and a cutting device. The grip may be coupled to a proximal end of the elongated member. A first end of the engaging portion may be coupled to a distal end of the elongated member. A second end of the engaging portion may turn in upon the engaging portion towards a first end of the engaging portion while still allowing trabeculae carneae to enter through an opening between the first and second ends. The cutting device may be positioned within an inner diameter of the engaging portion. The method may include positioning at least one trabeculae carneae in the inner diameter of the engaging portion. The method may include severing the at least one trabeculae carneae. The method may include increasing left ventricular compliance of the human heart. Severing trabeculae carneae in a left ventricle of a human heart may release elastic forces on the left ventricle. At least some of the trabeculae carneae may be severed adjacent an apex of the left ventricle.

In some embodiments, the method may include allowing trabeculae carneae to enter through an opening between the first and the second end of the engaging portion.

In some embodiments, the method may include inhibiting papillary muscles from entering through an opening between the first and the second end of the engaging portion.

In some embodiments, the cutting device may include a curved blade extending along at least a portion of the inner diameter.

In some embodiments, the cutting device, when activated, extends out of the elongated member and towards the inner diameter of the engaging portion. The cutting device may be biased to remain in the elongated member.

In some embodiments, the cutting device may include a plurality of blades positioned within the engaging portion which, when activated, extends out of the engaging portion. The plurality of cutting devices may be biased to remain in the engaging portion. In some embodiments, the plurality of blades may be activated using hydraulic pressure.

In some embodiments, the cutting device may include a laser. The laser may be positionable in the elongated member. The laser may include an optical fiber, a collimator, and a cylindrical lens. At least a portion of the laser may be translated along the elongated member.

In some embodiments, a laser may be directed through a plurality of openings positioned along the inner diameter of the engaging portion. The engaging portion may include light scattering elements in the interior of the engaging portion.

In some embodiments, the laser may include a Fresnel lens or Holographic Optical Element.

In some embodiments, a kit for cutting trabeculae carneae of a human heart may include a plurality of devices. Each device may include an elongated member, a grip coupled to a proximal end of the elongated member, and an engaging portion. A first end of the engaging portion may be coupled to a distal end of the elongated member. A second end of the engaging portion may turn in upon the engaging portion towards a first end of the engaging portion while still allowing trabeculae carneae to enter through an opening between the first and second ends. The device may include a cutting device. The cutting device may be positioned within an inner diameter of the engaging portion which severs trabeculae carneae during use. In some embodiments, the openings of the plurality of devices may include a range in sizes. The range may extend from an average small human trabeculae carneae to an average large human trabeculae carneae. The size of the opening may be less than the diameter of a human papillary muscle.

BRIEF DESCRIPTION OF THE DRAWINGS

Advantages of the present invention may become apparent to those skilled in the art with the benefit of the following detailed description of the preferred embodiments and upon reference to the accompanying drawings.

FIGS. 5A-B depict a device for cutting trabeculae carneae of a human heart with a cutting device which includes a plurality of blades positioned in an engaging portion of the device which, when activated, extends out of the engaging portion.

FIGS. 6A-B depict a device for cutting trabeculae carneae of a human heart with a cutting device which includes a plurality of blades positioned in an engaging portion of the device which, when activated using hydraulic pressure, extends out of the engaging portion.

Figure 1A:
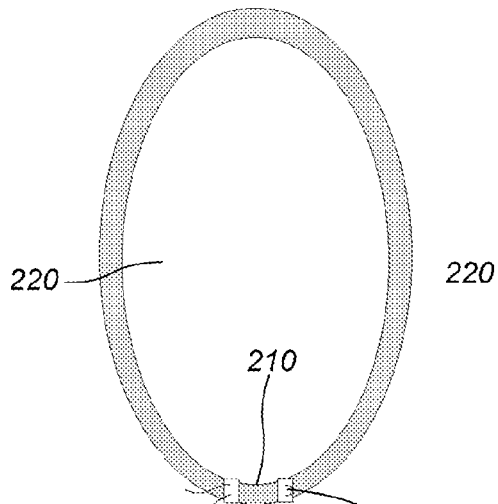
FIGS. 1A-H depict a diagram of a side view of an embodiment of a method for preparing a pathway for an instrument for cutting trabeculae in a left ventricle.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

\* \* \*

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112, paragraph six, interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The term "score" as used herein generally refers to cutting a thin line along the longitudinal axis of the left ventricle (apex to base) of variable depth and/or variable length causing minimal damage to the endocardium.

In some embodiments, trabeculae carneae of the left ventricle may be accessed via the aortic valve during open heart surgery. In other embodiments, trabeculae carneae of the left ventricle may be accessed through the mitral valve. In other embodiments, trabeculae carneae of the left ventricle may be accessed by piercing the apex of the left ventricle. In some embodiments, the one or more trabeculae carneae may be cut within the left ventricle.

The optimal number of trabeculae carneae to cut may vary. In some embodiments, the number of trabeculae carneae cut may vary from 1 to 80 trabeculae carneae within the left ventricle. The specific trabeculae carneae which are cut may also vary depending upon the subject's needs. In some embodiments, the trabeculae carneae which are cut may be located on at the apex, free wall, or septum of the left ventricle. In some embodiments, the trabeculae carneae which are cut may connect nets of trabeculae carneae to the ventricle wall, and cutting these trabeculae carneae may release the nets of trabeculae carneae from the ventricle wall. In some embodiments, the trabeculae carneae which are cut may be fibrotic and/or hypertrophied. There is precedence in nature for cutting trabeculae carneae to release elastic forces on the ventricle wall, as mammalian hearts with greater circumferential wall stress based on their ventricular chamber dimensions have greater numbers of left ventricular trabeculae carneae in total ($p=0.03$; Pearson correlation), and greater numbers of trabeculae carneae located at the apex and freewall ($p=0.02$; Pearson correlation), and those which connect nets of trabeculae carneae to the ventricle wall ($p=0.02$; Pearson correlation).

In some embodiments, a method may include ameliorating diastolic dysfunction of a human heart. In some embodiments, ameliorating diastolic dysfunction may include releasing elastic forces on the dysfunctional human heart. In some embodiments, ameliorating diastolic dysfunction may include cutting trabeculae carneae of a left ventricle of the human heart. The number of trabeculae carneae to be cut may vary from 1 to 80 trabeculae carneae within the left ventricle.

Figure 1B:
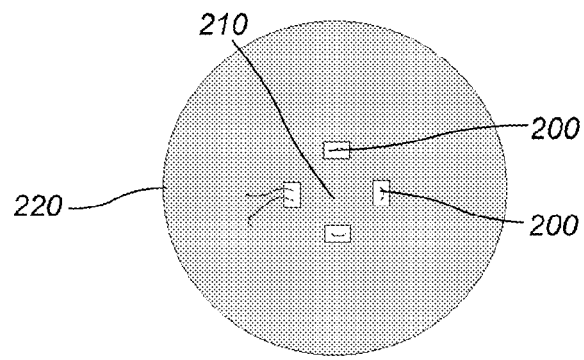
Figure 1C:
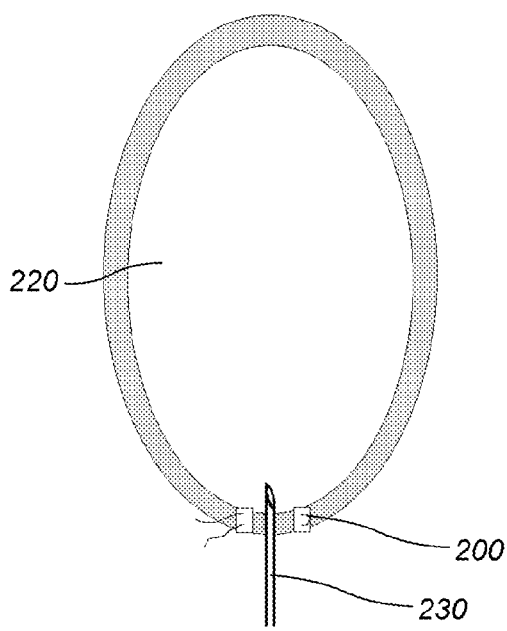
Figure 1D:
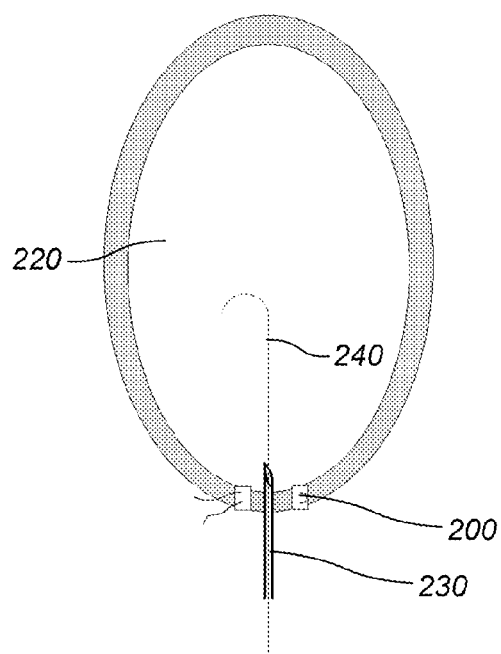
Figure 1E:
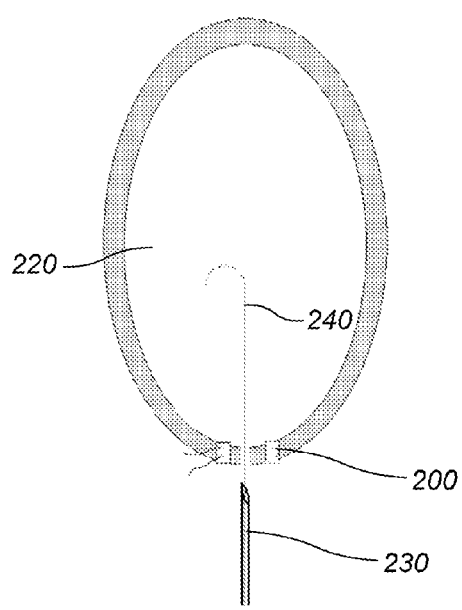
Figure 1F:
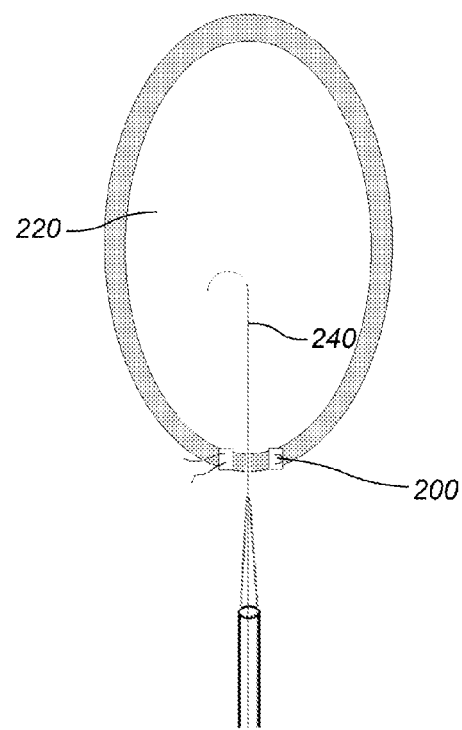
Figure 1G:
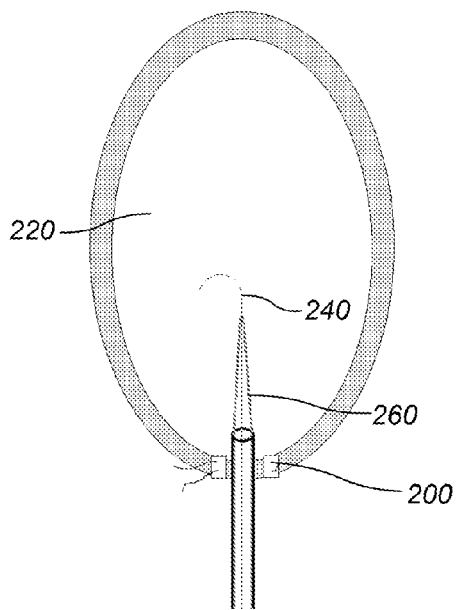
Figure 1H:
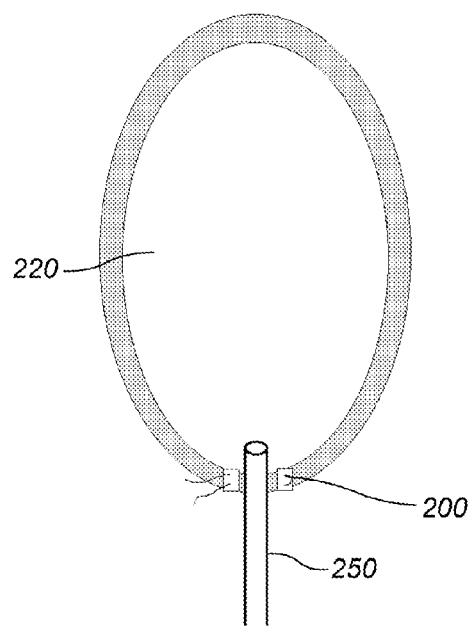

A left ventricle of a human heart may be accessed to accomplish procedures described herein using a number of different methods. In some embodiments, the left ventricle may be accessed through a valve (e.g., mitral valve) and/or an artery (e.g., femoral artery). In some embodiments, the left ventricle may be accessed directly through a ventricular wall of the heart. FIGS. 1A-H depict a diagram of a side view of an embodiment of a method for preparing a pathway for an instrument for cutting human trabeculae carneae in a left ventricle. In some embodiments, a method may include preparing a site at an apex of the left ventricle of the human heart. Preparing a site may include suturing pledgets 200 to apex 210 of left ventricle 220 (e.g. as depicted in FIGS. 1A-B). The pledgets may be used to control any discharges occurring during the procedure. The method may include inserting needle 230 into left ventricle 220 between two or more of the pledgets (e.g. as depicted in FIG. 1C). Guide wire 240 may be passed through needle 230 into left ventricle 220 (e.g. as depicted in FIG. 1D). After insertion of the guide wire the needle may be removed while leaving the guide wire positioned in the left ventricle (e.g. as depicted in FIG. 1E). Second conduit 250 (e.g., a guide catheter) may be inserted in left ventricle 220 (e.g., along guide wire 240). In some embodiments, entry device 260 may be employed in order to facilitate entry of second conduit 250 into left ventricle 220 through the opening created by needle 230 (e.g. as depicted in FIGS. 1F-G). Upon insertion of the second conduit, the guide wire and the entry device may be removed (e.g. as depicted in FIG. 1H). In some embodiments, a method may include rapidly pacing the heart (e.g., 200-220 beats per minute) for a short period of time essentially resulting in the heart appearing motionless so that trabecular cutting may be facilitated.

Current hypotheses of diastolic dysfunction and the elevated pressure-volume curve are related to changes in the compacted myocardial wall, where the myocardium thickens, becomes more fibrotic, undergoes titin expression changes shifting towards the stiffer N2B isoform, as well as endocardial ischemia and subsequent endocardial fibrosis. While all of these changes are likely to contribute to diastolic dysfunction, in some embodiments, trabeculae carneae are a contributor to the diastolic pressure-volume relationship. Trabeculae carneae may provide tensile strength to support the ventricular myocardium during diastole and to reduce the circumferential and meridional wall stress of the myocardium. Thus, it is anticipated that mammalian hearts which possess the highest left ventricular diastolic wall stress will have the more abundant trabeculae carneae.

Trabeculae carneae's role in supporting the ventricular myocardium was tested in 28 hearts from 10 mammalian species; pig (n=1), ferret (n=1), rabbit (n=2), cat (n=2), dog (n=3), pig (n=2), goat (n=2), sheep (n=5), cow (n=5) and horse (n=5). The number and location of trabeculae carneae were quantified within these 28 hearts, the number of trabeculae were normalized across all hearts, and mean normalized values of trabeculae carneae for each species were plotted against normalized values of circumferential wall stress calculated from M-mode echocardiographic chamber dimensions at end-diastolic for those species from the literature; cow, dog, horse, cat, rabbit, ferret, sheep, guinea pig (Boon, J A. Veterinary Echocardiography. 2nd ed. West Sussex: Wiley-Blackwell, 2011), sheep (Hallowell, *BMC Vet Res* 2012, 8:181), guinea pig (Soltysinska, *Exp Physiol* 2011, 96:647-663), pig (Lin, *Comp Med* 2002, 52:238-242), and goat (Hallowell, *BMC Vet Res* 2012, 8:181—Olsson, *Exp Physiol* 2001, 86:93-99—Leroux, *Vet Rec* 2012, 170:154). The relationship between trabeculae carneae and circumferential diastolic wall stress was analyzed using Pearson correlations.

Figure 2A:
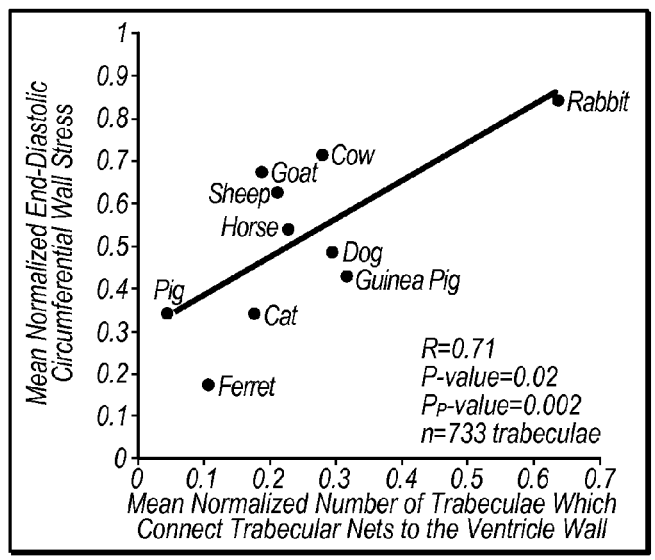
FIGS. 2A-C depict graphs of data on the correlation between trabeculae carneae and wall stress (WS) gathered in animal hearts and which supports that trabeculae function to support the heart during diastole.
Figure 2B:
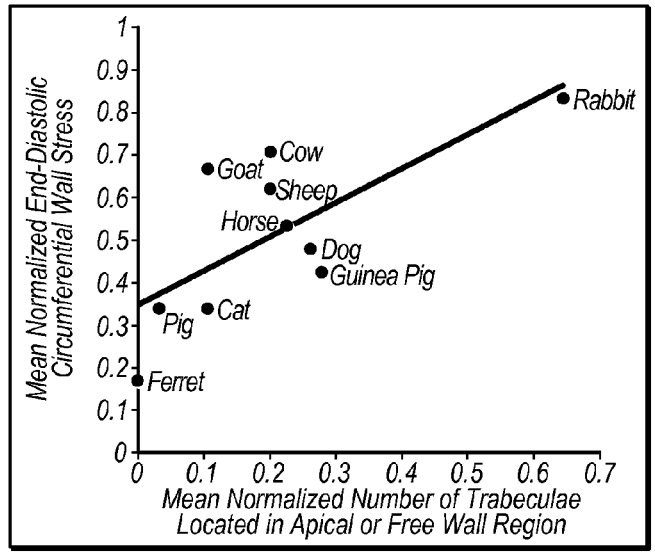
Figure 2C:
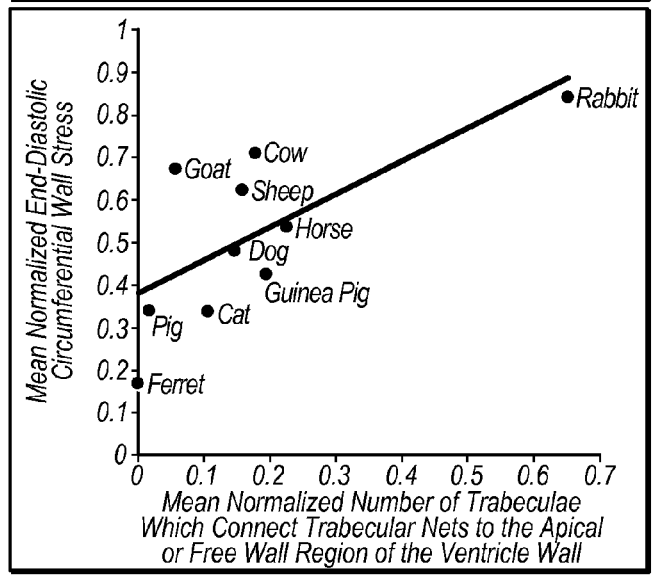
Figure 3:
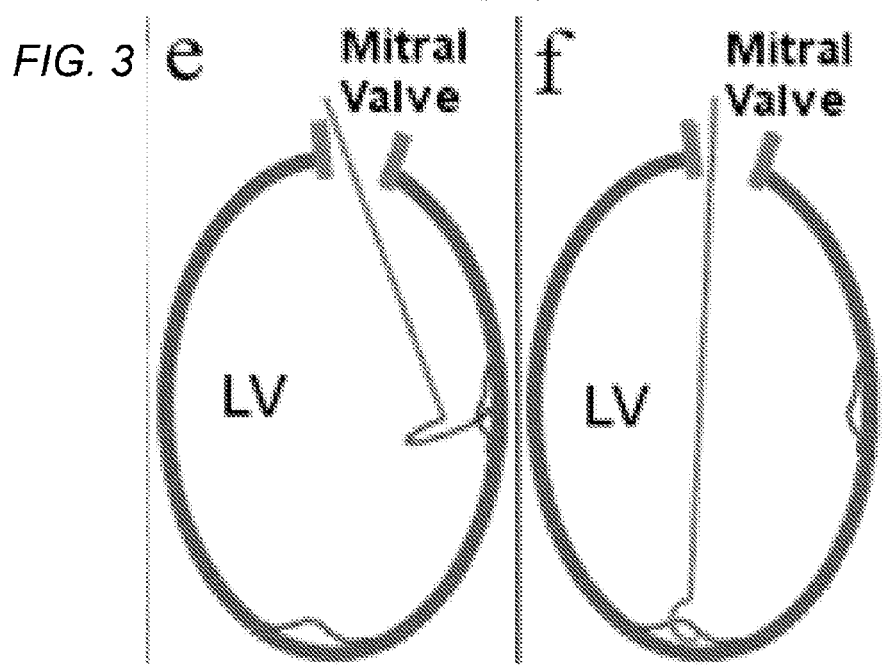
FIGS. 3A and D depicts a device for cutting trabeculae carneae of a human heart with a cutting device curved along an inner diameter of a curved engaging portion of the device.
FIGS. 3B-C depicts a device for cutting trabeculae carneae of a human heart with a cutting device curved along an inner diameter of a curved engaging portion of the device, wherein the engaging portion is at an approximately 90 degree angle to an elongated member of the device.
FIG. 3E depicts a device for cutting trabeculae carneae of a human heart with a cutting device curved along an inner diameter of a curved engaging portion of the device, wherein the engaging portion is at an approximately 90 degree angle to an elongated member of the device appropriate for severing trabeculae on the ventricular walls.
FIG. 3F depicts a device for cutting trabeculae carneae of a human heart with a cutting device curved along an inner diameter of a curved engaging portion of the device appropriate for severing trabeculae at the apex.

The total number of trabeculae carneae within the LV significantly correlated with LV end-diastolic circumferential wall stress ($p=0.03$, $R=0.70$). Trabeculae which connect to the ventricle wall on one end and to trabecular nets on the other end may have the greatest impact on normalizing wall stress since these trabecular nets substantially cross the ventricle while a trabeculae which connects to the ventricle wall only typically does not. Trabeculae which connect nets to the ventricle wall correlate significantly with LV end-diastolic circumferential wall stress across these 10 species ($R=0.71$, $p=0.02$, $n=733$ trabeculae, FIG. 2A). Trabeculae which connect to the ventricle wall in the septal region of the heart may be less important than trabeculae elsewhere in the ventricle, as the septum is buttressed by the RV and thus should require less tensile support than the apex (thinnest walled) and free wall regions. The subset of trabeculae which are located in the apical or free wall regions of the LV correlate significantly with LV end-diastolic circumferential wall stress across these 10 species ($R=0.72$, $p=0.02$, $n=602$ trabeculae, FIG. 2B). Trabeculae which satisfy both criteria (located in the apical or free wall region of the LV and connect the ventricle wall to trabecular nets) are also significantly correlated with LV end-diastolic circumferential wall stress ($R=0.70$, $p=0.02$, $n=316$ trabeculae, FIG. 2C).

However, the evolutionary basis for the existence of trabeculae carneae, which is to normalize left ventricular wall stress to prevent the development of myocardial hypertrophy and fibrosis in a normal heart, can evolve into a pathologic process in response to pressure or volume overload due to hypertension or valvular heart disease, respectively. In these conditions, the trabeculae carneae have been found to thicken and become more fibrotic, which contributes further to the reduced diastolic compliance. This pathologic response presents an opportunity for a new curative operation—the surgical resection of trabeculae carneae which will improve diastolic compliance where no previous medication or operation has been able to do so since the first description of diastolic dysfunction in the 1970s. By transecting free-running trabeculae carneae in 6 human cadaver hearts, the diastolic pressure-volume curve has been shifted toward improved compliance, which has not been achieved by any other therapeutic approach to date. Trabeculae carneae may therefore serve as a therapeutic avenue to improve LV compliance in patients with diastolic dysfunction. This macroscopic, physical approach is immediately accessible for patients with diastolic dysfunction. In some embodiments, a series of surgical tools using both physical means such as scapels and springs, and more precise cutting mechanisms such as lasers, as a new operative procedure may be used.

Hypertrophic obstructive cardiomyopathy (HOCM) presents with asymmetric left ventricular hypertrophy and diastolic dysfunction, but is a unique case which is more excessive than other etiologies. For this condition, the current clinical practice is myectomy, where a portion of the septum is removed from the left ventricle. The mechanism by which this procedure improves patient symptoms is relief of the obstruction. A myectomy may improve the diastolic compliance of the left ventricule, and this may be a mechanism which improves a patient's symptoms. Further, patients with HCM without obstruction but with debilitating symptoms due to diastolic dysfunction are currently not offered any left ventricular modifying procedure.

It is proposed that trabecular cutting and endocardial scoring represent new therapeutic options for these patients. In fact, myectomy probably increases diastolic compliance, currently not a hypothesized mechanism of benefit. In some embodiments, endocardial scoring may be used to improve diastolic compliance in a heart with hypertrophic cardiomyopathy.

In some embodiments, a method of ameliorating diastolic dysfunction may include positioning a second conduit in a human body such that a distal end of the second conduit is positioned in a left ventricle of a human heart. The method may include positioning a first conduit in the second conduit such that a distal end of the first conduit extends beyond the distal end of the second conduit into the left ventricle. The method may include activating a cutting device to sever at least one trabeculae. Severing trabeculae carneae in a left ventricle of a human heart may release pressure on the heart. At least some of the trabeculae carneae may be severed adjacent an apex of the left ventricle.

In some embodiments, ameliorating diastolic dysfunction may include positioning at least a distal end of a system 600 for cutting a trabeculae carneae in a left ventricle of a human heart. Different embodiments of the system are depicted in FIGS. 3-9. The system may include an elongated member 605, a grip 610, an engaging portion 620, and a cutting device 630. The grip may be coupled to a proximal end 640 of the elongated member 605. A first end 650 of the engaging portion 620 may be coupled to a distal end 660 of the elongated member. A second end 670 of the engaging portion 620 may turn in upon the engaging portion towards the first end of the engaging portion while still allowing trabeculae carneae to enter through an opening 680 between the first and second ends. The cutting device may be positioned within an inner diameter 690 of the engaging portion. The method may include positioning at least one trabeculae carneae in the inner diameter of the engaging portion. The method may include severing the at least one trabeculae carneae. The method may include increasing left ventricular compliance of the human heart. Severing trabeculae carneae in a left ventricle of a human heart may release elastic forces on the left ventricle. At least some of the trabeculae carneae may be severed adjacent an apex of the left ventricle.

In some embodiments, the method may include allowing trabeculae carneae to enter through an opening between the first and the second end of the engaging portion. In some embodiments, the method may include inhibiting papillary muscles from entering through an opening between the first and the second end of the engaging portion. For example, the internal diameter of the enclosed cutting portion may be about 3-5 mm such that trabeculae carneae may enter but other internal features of a human heart may not (e.g., papillary muscles).

In some embodiments, the cutting device may include a curved blade extending along at least a portion of the inner diameter. FIG. 3A depicts a device 600 for cutting trabeculae carneae of a human heart with a blade 630 curved along the inner diameter 690 of a curved engaging portion of the device. FIG. 3B depicts a device 600 for cutting trabeculae carneae of a human heart with a cutting device 630 curved along an inner diameter of a curved engaging portion 620 of the device, wherein the engaging portion is at an approximately 90 degree angle to an elongated member of the device. FIG. 3C and FIG. 3D show embodiments of trabecular cutting tools similar to those depicted in FIG. 3A and FIG. 3B. The engaging portion may be oriented at any angle relative to the elongated member of the device. The angle may be dependent upon the ease of use during a procedure on the heart. As for example what angle is best for a user to reach the trabeculae carneae the user wishes to sever. In some embodiments, at least the juncture between the elongated member and the engaging portion may include an adjustable joint such that a user may adjust the angle between the elongated member and the engaging portion. The adjustable joint may be a substantially pliable portion. The pliable portion may be pliable enough to allow a user to adjust the angle but not pliable enough that the angle may be accidentally changed during normal usage. The adjustable joint may include any one of several known mechanical joints which are adjustable. A mechanical joint may include a method of "locking" the joint once the desired angle is achieved, such that movement is then inhibited.

Figure 4:
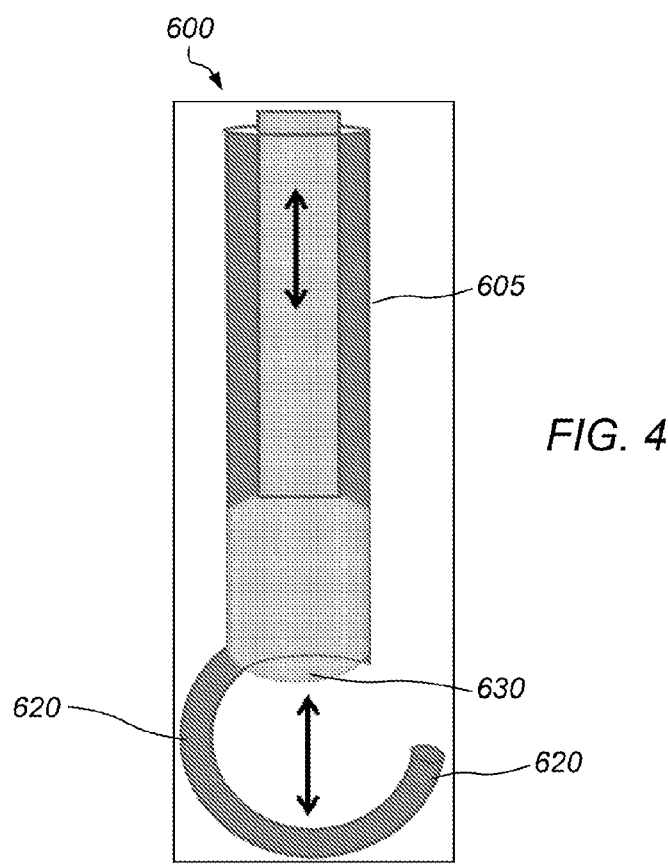
FIG. 4 depicts a device for cutting trabeculae carneae of a human heart with a cutting device which extends out of an elongated member towards an inner diameter of a curved engaging portion of the device.

In some embodiments, the cutting device, when activated, extends out of the elongated member and towards the inner diameter of the engaging portion. The cutting device may be biased to remain in the elongated member. FIG. 4 depicts a device 600 for cutting trabeculae carneae of a human heart with a cutting device 630 which extends out of an elongated member towards an inner diameter of a curved engaging portion of the device. The cutting device may be biased towards remaining in the elongated member until activated. The cutting device may be biased by a force exerted by, for example, a spring or flexible member. The cutting device may include an appropriately shaped blade. The blade may be shaped such that the contour of the blade is complementary to the curve of the inner diameter of the engaging portion. For example, the blade may have a convex curvature which is complementary to the concave curvature of the engaging portion.

In some embodiments, the cutting device may include a plurality of blades positioned at least partially in the engaging portion which, when activated, extend out of the engaging portion. The plurality of cutting devices may be biased to remain in the engaging portion. FIGS. 5A-B depict a device for cutting trabeculae carneae of a human heart with a cutting device 630 which includes a plurality of blades 630*a-d* positioned in an engaging portion 620 of the device 600 which, when activated, extends out of the engaging portion. The cutting device may be biased towards remaining in the elongated member until activated. The cutting device may be biased by a force exerted by, for example, a spring 700 or flexible member. The cutting devices may be coupled to and activated by a cable 710 extending through the elongated member. In some embodiments, the plurality of blades may be activated using hydraulic pressure. FIGS. 6A-B depict a device 600 for cutting trabeculae carneae of a human heart with a cutting device 630 which includes a plurality of blades positioned in an engaging portion 620 of the device which, when activated using hydraulic pressure, extends out of the engaging portion. The hydraulic pressure may temporarily overcome the force exerted by the springs 700 such that the cutting devices 630 extend out of the engaging portion. In some embodiments, circular blades attached to pistons are positioned inside of the hook adjacent to a sealed hydraulic chamber within the handle and hook. When pressure is increased within the sealed hydraulic chamber, the pistons are pushed out of the hydraulic chamber towards the center of the hook, causing the blades attached to the pistons to deploy through a slit in the inside of the hook to cut a trabeculae carneae within the hook. When the pressure is reduced within the hydraulic chamber, springs attached to the pistons return the pistons and blades to the un-deployed position. The arrows represent hydraulic pressure within the hydraulic chamber.

Figure 7:
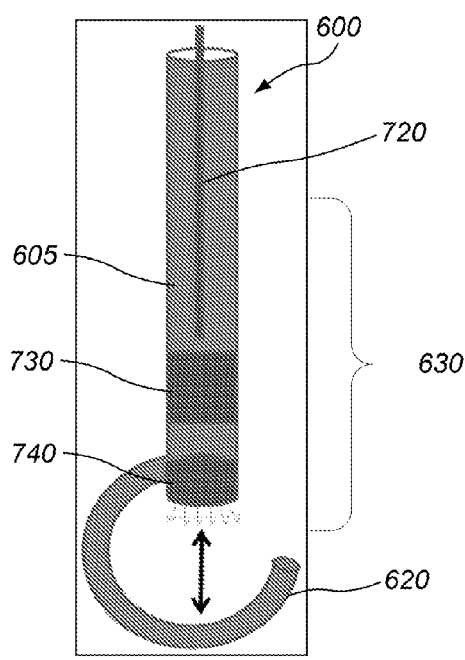
FIG. 7 depicts a device for cutting trabeculae carneae of a human heart with a cutting device, wherein the cutting device includes a laser positionable in an elongated member of the device.

In some embodiments, the cutting device may include a laser. FIG. 7 depicts a device 600 for cutting trabeculae carneae of a human heart with a cutting device 630, wherein the cutting device includes a laser positionable in an elongated member 605 of the device. The laser may be positionable in the elongated member. The laser may include an optical fiber 720, a collimator 730, and a cylindrical lens 740. At least a portion of the laser may be translated along the elongated member. In some embodiments, laser radiation travels down the optical fiber and through the collimator and cylindrical lens. The optical fiber, collimator, and cylindrical lens may be translated relative to the engaging portion to facilitate cutting of a trabeculae carneae in the engaging portion.

Figure 8:
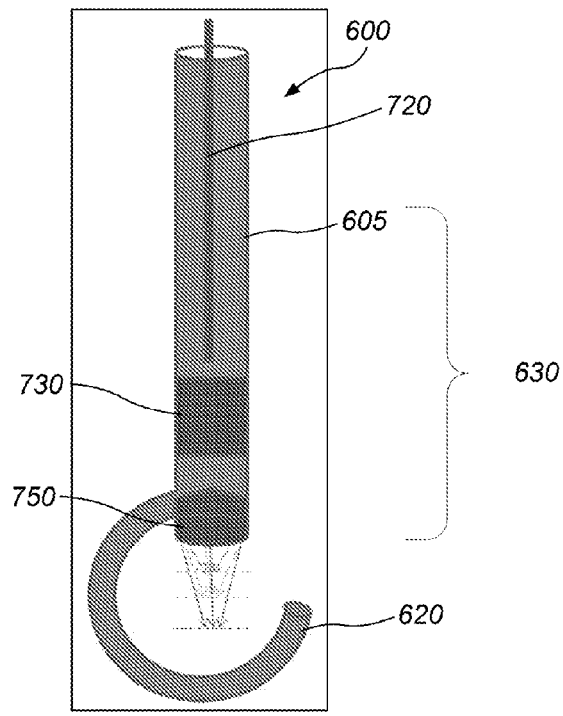
FIG. 8 depicts a device for cutting trabeculae carneae of a human heart with a cutting device, wherein the cutting device includes a laser including a Fresnel lens or Holographic Optical Element and wherein the laser is of variable wavelength.

In some embodiments, the laser may include a Fresnel lens or holographic optical element, and the laser may be of variable wavelength. FIG. 8 depicts a device for cutting trabeculae carneae of a human heart with a cutting device, wherein the cutting device includes a laser including a Fresnel lens 750. In some embodiments, laser radiation of variable wavelength travels down an optical fiber 720, through a collimator 730 and then through a Fresnel lens 750 or a holographic optical element. The Fresnel lens or holographic optical element will focus the laser radiation to different focal depths for different wavelengths of radiation. These variable focal depths will facilitate cutting of a trabeculae carneae within the hook without requiring translation of the optics relative to the hook. The arrows represent laser radiation of different wavelengths.

Figure 9:
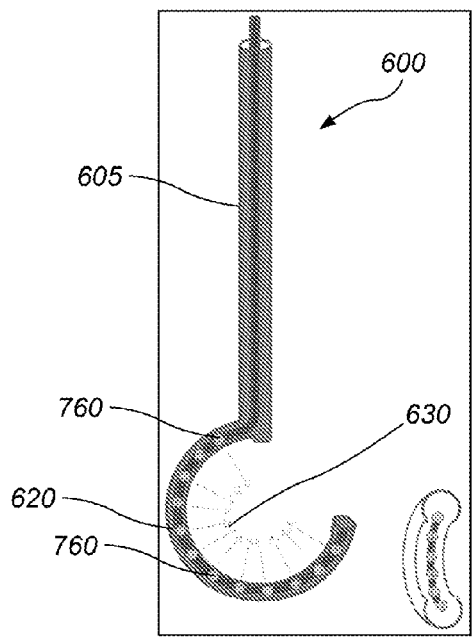
FIG. 9 depicts a device for cutting trabeculae carneae of a human heart with a cutting device, wherein the cutting device includes a laser directed through a plurality of openings positioned along the inner diameter of the engaging portion.
Figure 10:
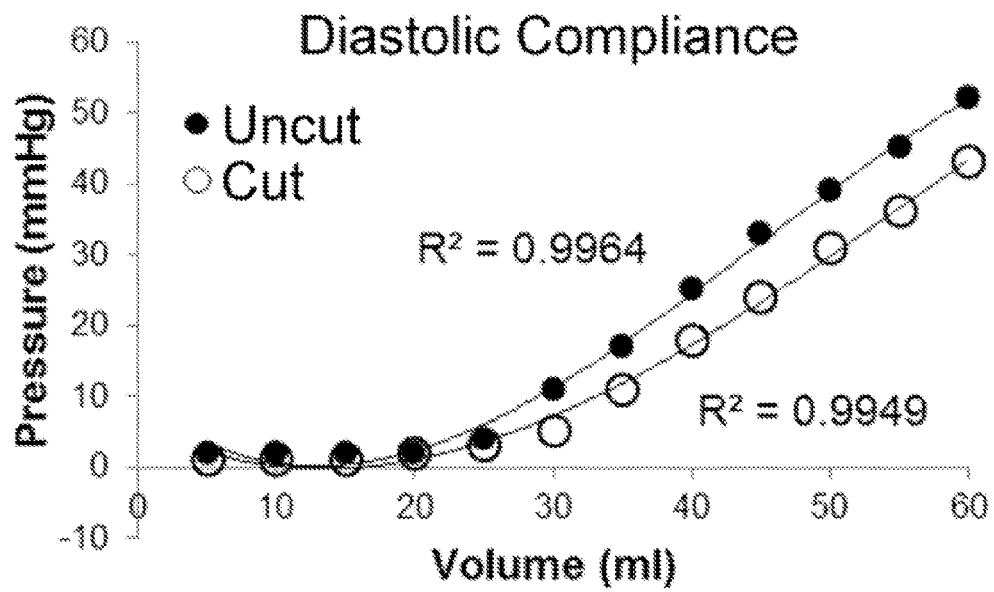
FIGS. 10-15 depict graphs of case studies wherein a system and/or method for cutting trabeculae carneae was used for increasing diastolic compliance in a hypertrophied cadaver heart. Mean data for these 6 case studies are shown in FIG. 16.
Figure 11:
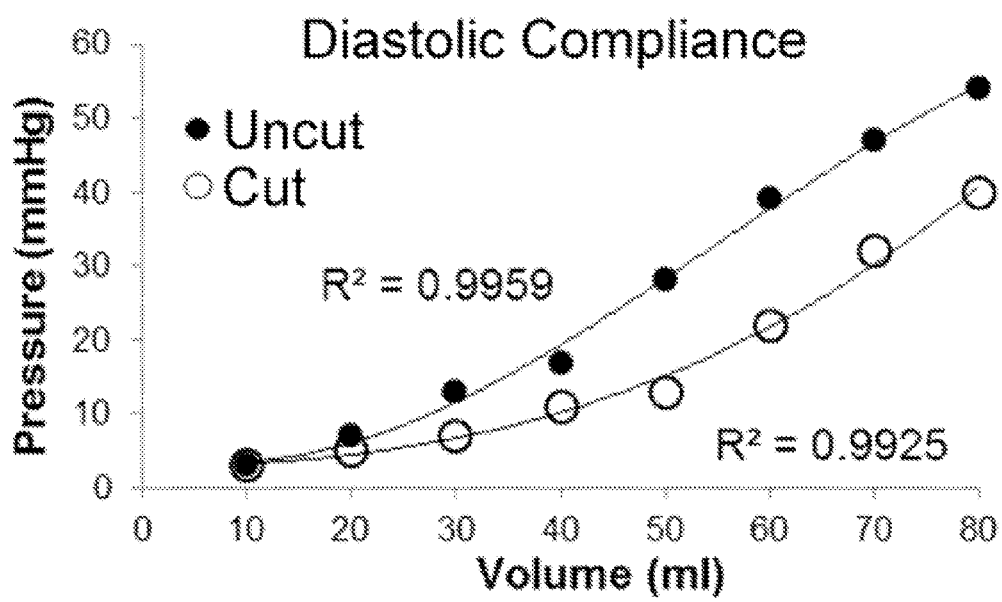
Figure 12:
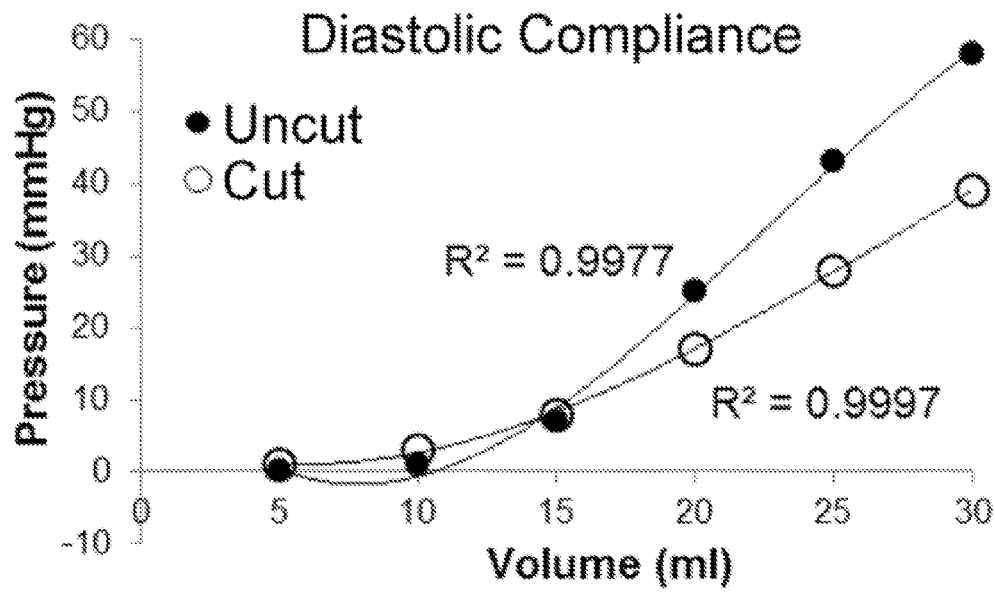
Figure 13:
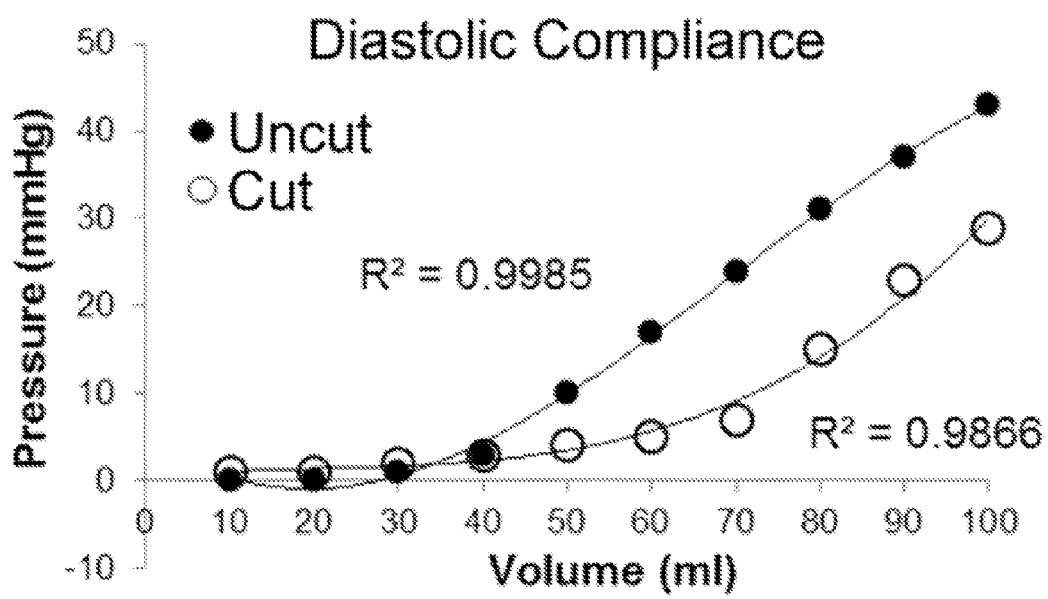
Figure 14:
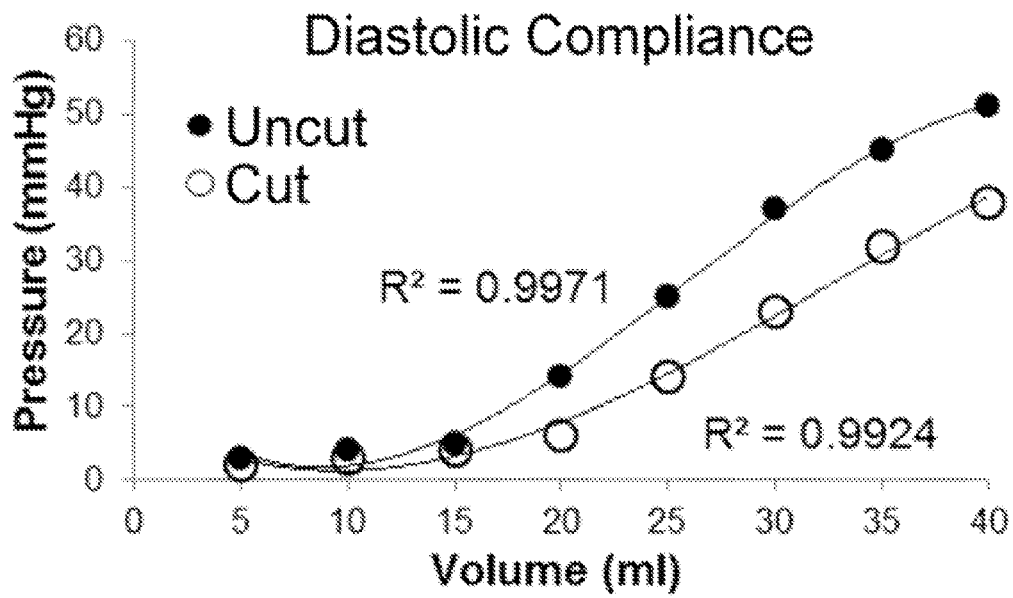
Figure 15:
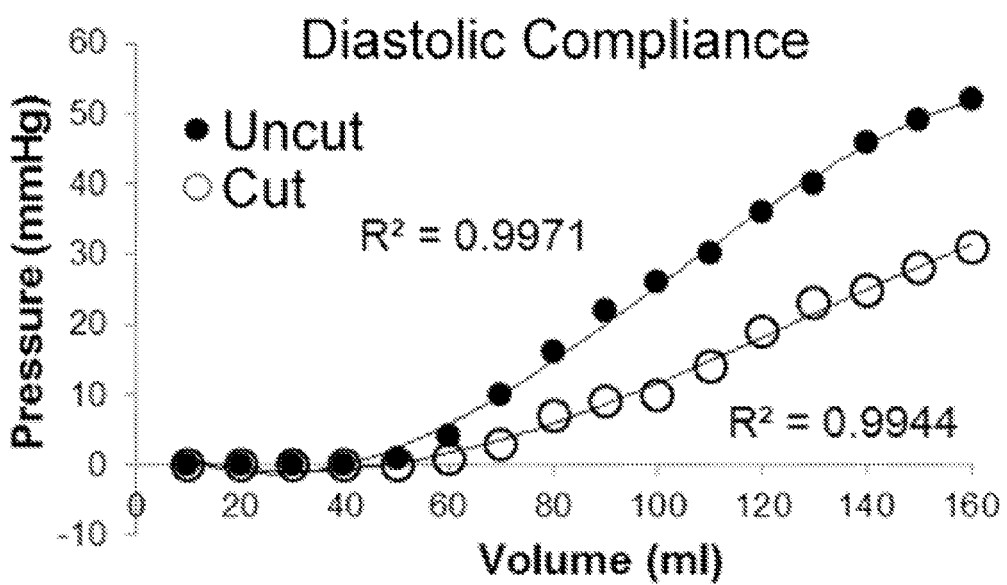

In some embodiments, a laser may be directed through a plurality of openings 760 positioned along the inner diameter of the engaging portion 620. The engaging portion may include light scattering elements in the interior of the engaging portion. FIG. 9 depicts a device 600 for cutting trabeculae carneae of a human heart with a cutting device 630, wherein the cutting device includes a laser directed through a plurality of openings 760 positioned along the inner diameter of the engaging portion. In some embodiments, laser radiation travels down an optical fiber extending through the engaging portion. The optical fiber may have scattering centers along the curve of the hook to scatter laser radiation out of the optical fiber. The inside of the hook is made of a reflective material to direct the scattered laser radiation through a slit on the inside of the hook, and onto a trabeculae carneae within the hook to make the cut. The arrows represent laser radiation.

In some embodiments, a kit for cutting trabeculae carneae of a human heart may include a plurality of devices. Each device may include an elongated member, a grip coupled to a proximal end of the elongated member, and an engaging portion. A first end of the engaging portion may be coupled to a distal end of the elongated member. A second end of the engaging portion may turn in upon the engaging portion towards a first end of the engaging portion while still allowing trabeculae carneae to enter through an opening between the first and second ends. The device may include a cutting device. The cutting device may be positioned within an inner diameter of the engaging portion which severs trabeculae carneae during use. In some embodiments, the openings of the plurality of devices may include a range of sizes. The range may extend from an average small human trabeculae carneae to an average large human trabeculae carneae. The size of the opening may be less than the diameter of a human papillary muscle. Limiting the size of the opening may have several advantages. Advantages may include inhibiting structural features of the heart other than human trabeculae carneae from entering the opening and being inadvertently severed. This is important in that inadvertent damage to the heart does not occur during a procedure.

EXAMPLES

Figure 16:
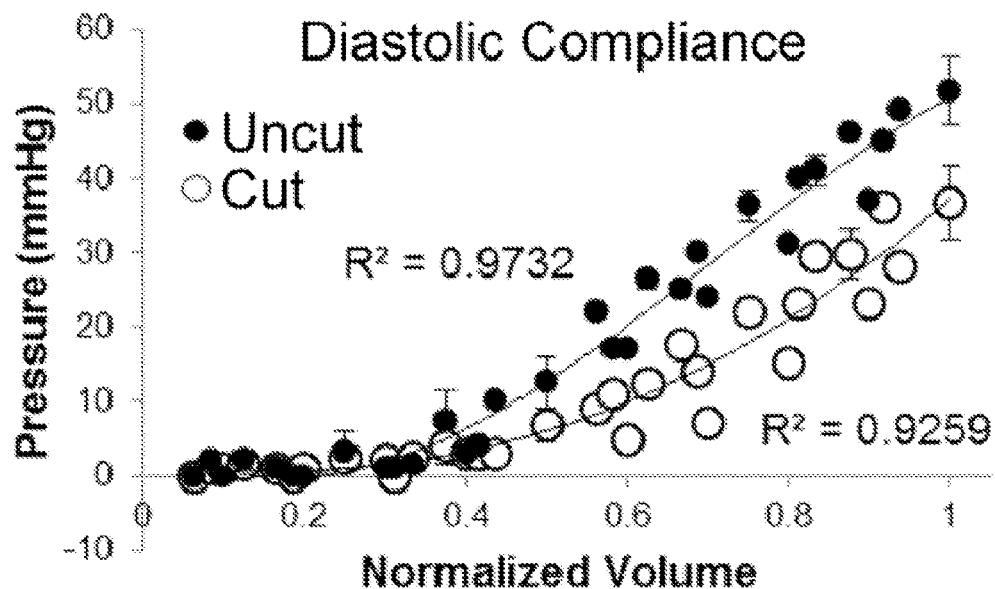

In some embodiments, trabeculae carneae are cut within the left ventricle to acutely increase LV compliance, improve patient symptoms and reduce hospital admissions due to diastolic dysfunction. Several successful reductions to practice were carried out in cadaver hearts as demonstrated in FIGS. 10-15, with mean data shown in FIG. 16. Six isolated human hearts were obtained and LV diastolic compliance was measured at baseline, and following the cutting of trabeculae carneae within the LV. The ex vivo human hearts used were perfused via both coronary arteries at 37 degrees centigrade with saline to maintain body temperature. The left atria were opened to allow placement of a balloon into the LV cavity through the mitral valve. The balloon was capped with an air- and fluid-tight seal and the heart was suspended, and micro-manometer pressure sensor was placed inside the balloon. As known amounts of saline were added to the balloon, the resulting pressure was measured to generate the data points that allowed construction of the diastolic pressure-volume relation allowing calculation of compliance. FIGS. 10-15 depict graphs of case studies wherein a system and/or method for cutting trabeculae carneae was used for increasing diastolic compliance in a hypertrophied cadaver heart. The baseline data is plotted relative to left ventricular diastolic compliance following cutting of the trabeculae carneae. As is visibly evident, there was a marked acute increase in left ventricular compliance demonstrating a successful reduction to practice of our approach in all six hearts. To analyze these shifts in compliance for statistical significance, FIG. 16 shows grouped data for all 6 hearts, with each heart normalized by volume. Within-subject changes in pressure (uncut minus cut) were computed and we assessed the significance of the relation between changes in pressure and volume using a repeated measures mixed-effects cubic model and assuming an (ar1) autocorrelation matrix. The shift in compliance observed in these hearts is significant ($p<0.001$).

Figure 17:
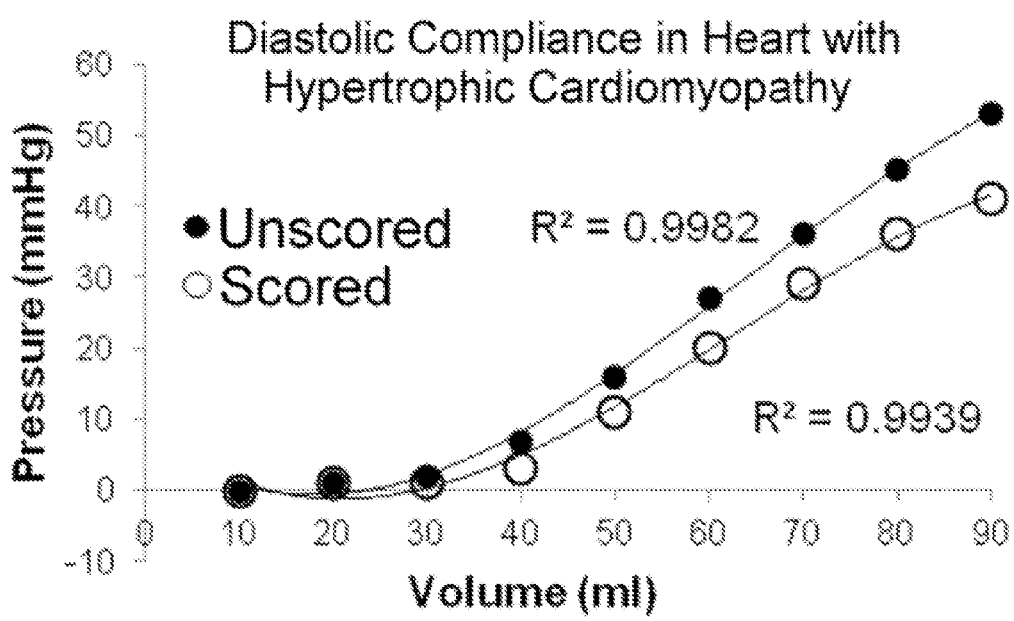
FIG. 17 depicts a graph of a case study wherein a system for scoring human endocardium tissue was used for increasing left ventricular compliance in a subject with hypertrophic cardiomyopathy.

Improved diastolic compliance in a cadaver heart with hypertrophic cardiomyopathy via endocardial scoring was demonstrated. The myocardium of the left ventricle was scored longitudinally from apex to base (below mitral valve) in each of the four quadrants of the left ventricle with an average scoring depth of 6.7 mm. The myocardial thickness was asymmetrical, ranging from 34 mm near the septum to 19 mm near the free wall. FIG. 17 depicts a graph of a case study wherein a system for scoring human endocardium tissue was used for increasing left ventricular compliance in a subject. The baseline data is plotted relative to left ventricular diastolic compliance following scoring of the human endocardium tissue.

Figure 18:
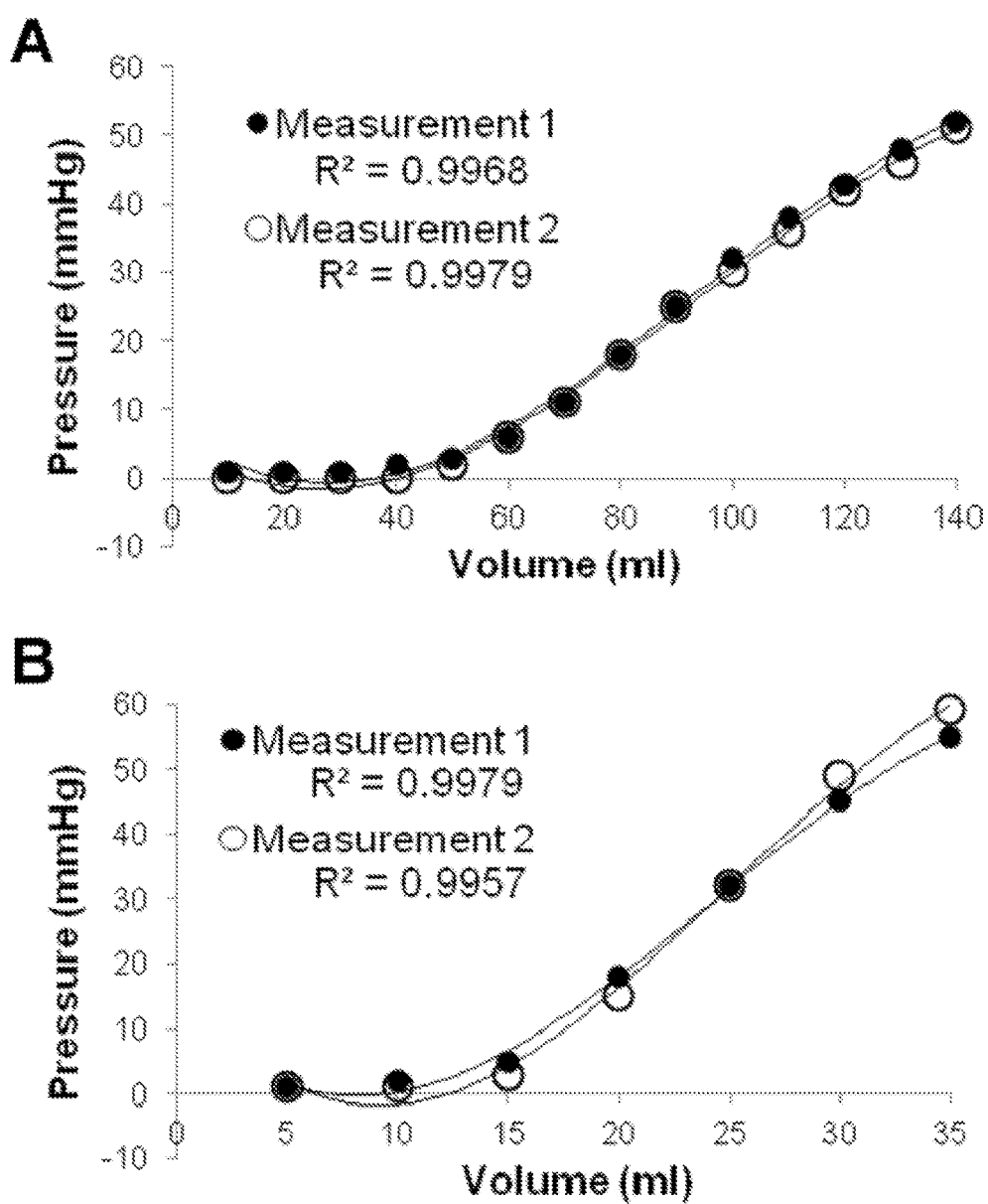
FIG. 18 depicts graphs of two control cadaver human hearts for diastolic compliance measurement.

Two control cadaver hearts (FIGS. 18A-B) which had baseline compliance measured were investigated, followed by a second measurement of compliance, without cutting trabeculae. In both controls, the compliance was not changed between the first and second measurement, demonstrating that the diastolic compliance curve does not change in lieu of trabecular cutting.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of ameliorating diastolic dysfunction, comprising:
    positioning at least a distal end of a system for cutting a trabeculae carneae in a left ventricle of a human heart, wherein the system comprises:
        an elongated member;
        a grip coupled to a proximal end of the elongated member;
        an engaging portion, wherein a first end of the engaging portion is coupled to a distal end of the elongated member, wherein a second end of the engaging portion turns in upon the engaging portion towards the first end of the engaging portion while still allowing trabeculae carneae to enter through an opening between the first and second ends; and
        a cutting device comprising an optical fiber, a portion of which is positioned within the engaging portion;
    positioning at least one trabeculae carneae through the opening of the engaging portion;
    severing the at least one trabeculae carneae; and
    increasing left ventricular compliance of the human heart.

2. The method of claim 1, further comprising inhibiting papillary muscles from entering through the opening between the first and the second end of the engaging portion.

3. The method of claim 1, wherein the cutting device comprises at least a portion of the fiber optic cable positionable in the elongated member.

4. The method of claim 1, wherein the cutting device comprises a fiber optic cable which directs a laser through a plurality of openings positioned along an inner diameter of the engaging portion.

5. The method of claim 4, wherein the engaging portion comprises light scattering elements in the interior of the engaging portion.

\* \* \* \* \*